United States Patent
Meerholz et al.

(10) Patent No.: US 7,592,414 B2
(45) Date of Patent: Sep. 22, 2009

(54) MATERIALS THAT CAN BE STRUCTURED, METHOD FOR PRODUCING THE SAME AND THEIR USE

(75) Inventors: Klaus Meerholz, Rösrath (DE); Michael Bayerl, Türkheim (DE); Florian Bielefeldt, Basel (CH); Thomas Braig, Düsseldorf (DE); Markus Gross, Sauerlach (DE); David Müller, Köln (DE); Oskar Nuyken, Munich (DE); Hubert Spreitzer, Viernheim (DE)

(73) Assignee: Merck Patent GmbH (DE)

( * ) Notice: Subject to any disclaimer, the term of this patent is extended or adjusted under 35 U.S.C. 154(b) by 135 days.

(21) Appl. No.: 10/343,465

(22) PCT Filed: Aug. 1, 2001

(86) PCT No.: PCT/EP01/09176

§ 371 (c)(1),
(2), (4) Date: Oct. 23, 2003

(87) PCT Pub. No.: WO02/10129

PCT Pub. Date: Feb. 7, 2002

(65) Prior Publication Data

US 2004/0054152 A1 Mar. 18, 2004

(30) Foreign Application Priority Data

Aug. 1, 2000 (DE) ................. 100 37 391

(51) Int. Cl.
C09K 11/06 (2006.01)
H01L 51/00 (2006.01)
H01L 51/50 (2006.01)

(52) U.S. Cl. .............. 528/417; 428/917; 313/504; 257/40; 257/E51.031; 257/E51.049; 257/E51.05; 252/301.16; 252/301.35; 585/19; 585/26; 585/27; 549/330; 549/510; 546/49

(58) Field of Classification Search .......... 528/417
See application file for complete search history.

(56) References Cited

U.S. PATENT DOCUMENTS

| | | | |
|---|---|---|---|
| 5,281,489 A * | 1/1994 | Mori et al. .......... | 428/690 |
| 5,518,824 A * | 5/1996 | Funhoff et al. ........ | 428/690 |
| 5,621,131 A | 4/1997 | Kreuder et al. ........ | 558/46 |
| 5,840,217 A | 11/1998 | Lupo et al. .......... | 252/583 |
| 5,861,219 A * | 1/1999 | Thompson et al. ...... | 428/690 |
| 5,922,481 A * | 7/1999 | Etzbach et al. ........ | 428/690 |
| 2002/0028347 A1* | 3/2002 | Marrocco et al. ...... | 428/690 |
| 2002/0106529 A1* | 8/2002 | Okunaka et al. ....... | 428/690 |
| 2003/0064248 A1* | 4/2003 | Wolk et al. .......... | 428/690 |

FOREIGN PATENT DOCUMENTS

| | | |
|---|---|---|
| DE | 4422332 | 1/1996 |
| DE | 19744792 | 4/1999 |
| DE | 19846766 | 4/2000 |
| DE | 19846767 | 4/2000 |
| DE | 19846768 | 4/2000 |
| EP | 0676461 B1 | 8/2002 |
| WO | 94/05045 | 3/1994 |
| WO | 95/31833 | 11/1995 |
| WO | 96/19792 | 6/1996 |
| WO | 98/03566 | 1/1998 |
| WO | 98/27136 | 6/1998 |
| WO | 98/48433 | 10/1998 |
| WO | 98/53510 | 11/1998 |
| WO | 99/10939 | 3/1999 |

OTHER PUBLICATIONS

Bayerl et al., "Crosslinkable hole-transport materials . . . ", Macromol. Rapid Commun., vol. 20, No. 4, pp. 224-228 (1999).*
Klarner et al., "Cross-linkable Polymers Based on Dialkylfluorenes", Chem. Mater. 11(7), pp. 1800-1805 (1999).*
U.S. Appl. No. 60/211,108, filed Jun. 2000.*

* cited by examiner

Primary Examiner—Marie R. Yamnitzky
(74) Attorney, Agent, or Firm—Connolly Bove Lodge & Hutz LLP

(57) ABSTRACT

The invention provides low molecular weight or polymeric organic materials in which at least one hydrogen atom is replaced by a group of the formula (A)

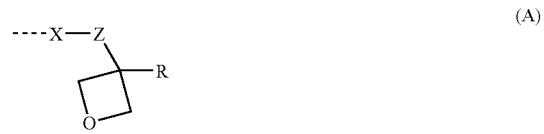

where R is alkyl group, alkoxyalkyl group, alkoxy group, thioalkoxy group, aryl group or alkenyl group, in each of which one or more hydrogen atoms may be replaced and one or more nonadjacent carbon atoms may be replaced.

Z is —O—, —S—, —CO—, —COO—, —O—CO— or a bivalent group —$(CR_1R_2)_n$— in which $R_1$ and $R_2$ are hydrogen, alkyl, alkoxy, alkoxyalkyl or thioalkoxy group, aryl or alkenyl, in each of which one or more hydrogen atoms may be replaced and one or more nonadjacent carbon atoms may be replaced, and n is an integer from 1 to 20.

X is a bivalent group —$(CR_1R_2)_n$— and, with the proviso that the number of these A groups is limited by the maximum number of available substitutable hydrogen atoms. The invention also relates to their use for producing optionally multilayered structured light emitting diodes, lasers, solar cells, waveguides or integrated circuits.

16 Claims, 2 Drawing Sheets

MATERIALS THAT CAN BE STRUCTURED, METHOD FOR PRODUCING THE SAME AND THEIR USE

For a few years, there has existed a rapidly growing needs for organic materials which are required for use in electronic applications. Typical applications are those in organic (OLED) or polymeric light emitting diodes (PLED) (cf., for example, EP-A-0 676 461, WO 98/27136), organic solar cells (cf., for example, WO 98/48433, WO 94/05045), organic lasers (for example WO 98/03566) and also in organic circuits (ICs) (for example WO 95/31833, WO 99/10939).

The use of materials is described [lacuna] the abovementioned applications and patents and the references cited therein and will not be further reinforced here. With regard to the use, these texts are incorporated in the present invention by way of reference.

Compounds used in the abovementioned fields of application are both low molecular weight and polymeric compounds.

For organic and polymeric light emitting diodes and laser applications, these include both active materials (i.e. light emitting substances) and materials for further auxiliary layers, i.e., for example, charge transport layers having certain optical properties.

For use in the fields of application of solar cells and organic switching elements, there is a preference and a requirement for organic semiconductors and insulators, and therefore in general for charge transport materials having different transport properties.

In all of these applications, typically used compounds in the spectrum of high molecular weight compounds are conjugated or at least partially conjugated polymers. Typical representatives of conjugated polymers are poly(p-phenylene-vinylene) [PPV] or poly-p-phenylene [PPP]. When the PPP structure is composed predominantly of fluorene building blocks, these materials are also referred to as polyfluorenes. When the PPP structure predominantly contains spiro-9,9'-bifluorene units, these are known as polyspiros.

For the purposes of this invention, partially conjugated polymers are those substances which either have mainly conjugated segments in the main chain which are interrupted by nonconjugated segments, or are those which have relatively long conjugated segments in the side chain.

On the other hand, low molecular weight compounds are already successfully used in some of the abovementioned fields of application.

Among the low molecular weight compounds, those having aromatic π-systems (aromatics) have gained particular importance. In addition to 2-dimensional aromatics, for example triphenylene derivatives (DE-A-4422332), aromatics having a 3-dimensional spatially extended structure in particular have proven advantageous. Typical representatives are compounds which are based on spirobifluorene (EP-A-676461), triptycene or iptycene (DE-A-19744792).

Although different types of substance already find use in all of these applications, the development of these types of compound should in no way be regarded as being complete.

For instance, there is firstly a strong pressure to lengthen the operating lifetime of the compounds in the respective applications, and secondly structuring in certain applications is also an unsolved problem.

Depending on the field of use, structuring is a very important criterion: in displays (based on OLED or PLED technology), for example, the individual pixels have to be generated. Of course, a similar problem also presents itself in generating organic circuits and sometimes also in structuring organic solar cell panels or laser arrays. Customarily, these structurings are carried out at the "feeds", i.e., for example, at the electrodes. This may be effected, for example, using shadow masks of the template type; however, for industrial mass production this may result in distinct disadvantages: after being used once or more than once, the masks are unusable owing to deposit formation and have to be regenerated in a costly and inconvenient manner.

A further possibility for structuring also involves applying the active layer (here: either the light-emitting layer in OLEDs/PLEDs and lasers or charge transport layers in all applications) directly in structured form. Since this presents considerable problems is understandable from the dimensions alone: structures in the range from a few tens of μm have to be generated at layer thicknesses in the range from approx. 100 nm to a few μm. Printing processes (such as offset printing, inkjet printing, or similar techniques) may possibly be suitable for this purpose, although no such process is yet suitable for production. In this case also (in the field of OLEDs), the mask technology already outlined above for the electrodes is used. However, this is clearly accompanied in this case by the above-outlined problems of deposit formation.

Polym. Materials, Science and Engineering 80, 122 (1999) discloses N,N,N',N'-tetraphenylbenzidines functionalized by oxetane groups whose crosslinking can be photoinduced. The abovementioned class of compounds are used as structurable hole conductors in organic light emitting diodes (OLEDs), so that structured OLEDs can be obtained.

It is therefore an object of the present invention to provide structurable materials which are suitable for use in structured devices, such as OLEDs, PLEDs, organic lasers, organic switching elements and organic solar cells, and result in the property profile of these devices at least being retained.

It has now been found that, surprisingly, organic materials can be structured in the above-listed applications when they contain at least one oxetane group capable of crosslinking whose crosslinking reaction can be initiated and controlled in a targeted manner. This may be carried out under suitable conditions in such a way that no impairment of the other device characteristics occurs, but so that the structuring is distinctly simplified or is made possible in the first place.

The invention therefore provides low molecular weight or polymeric organic materials which are used in the abovementioned electronic applications, in which at least one hydrogen atom is replaced by a group of the formula (A)

(A)

where

R is a straight-chain, branched or cyclic alkyl, alkoxyalkyl, alkoxy or thioalkoxy group having from 1 to 20 carbon atoms, $C_4$-$C_{18}$-aryl or $C_2$-$C_{10}$-alkenyl, in each of which one or more hydrogen atoms may be replaced by halogen, such as Cl or F, or CN, and one or more nonadjacent carbon atoms may be replaced by —O—, —S—, —CO—, —COO— or —O—CO—, Z is —O—, —S—, —CO—, —COO—, —O—CO— or a bivalent group —$(CR_1R_2)_n$— in which $R_1$ and $R_2$ are each independently hydrogen, a straight-chain, branched or cyclic alkyl, alkoxy, alkoxyalkyl or thioalkoxy group having from 1 to 20 carbon atoms, $C_4$-$C_{18}$-aryl or $C_2$-$C_{10}$-alkenyl, in each of which one or more hydrogen atoms may be replaced by halogen, such as Cl or F, or CN, and one or more nonadjacent carbon atoms may be replaced by —O—, —S—, —CO—, —COO— or —O—CO—, X is a bivalent group —$(CR_1R_2)_n$— in which $R_1$ and $R_2$ are each independently hydrogen, a straight-chain, branched- or cyclic alkyl, alkoxy, alkoxyalkyl- or thioalkoxy group having from 1 to 20 carbon atoms, $C_4$-$C_{18}$-aryl or $C_2$-$C_{10}$-alkenyl, in each of which one or more hydrogen atoms may be replaced by halogen, such as Cl or F, or CN, and n is an integer from 1 to 20, preferably from 3 to 10, in particular 3 or 6, with the proviso that the number of these A groups is limited by the maximum number of available, i.e. substitutable, hydrogen atom.

Figure 1:
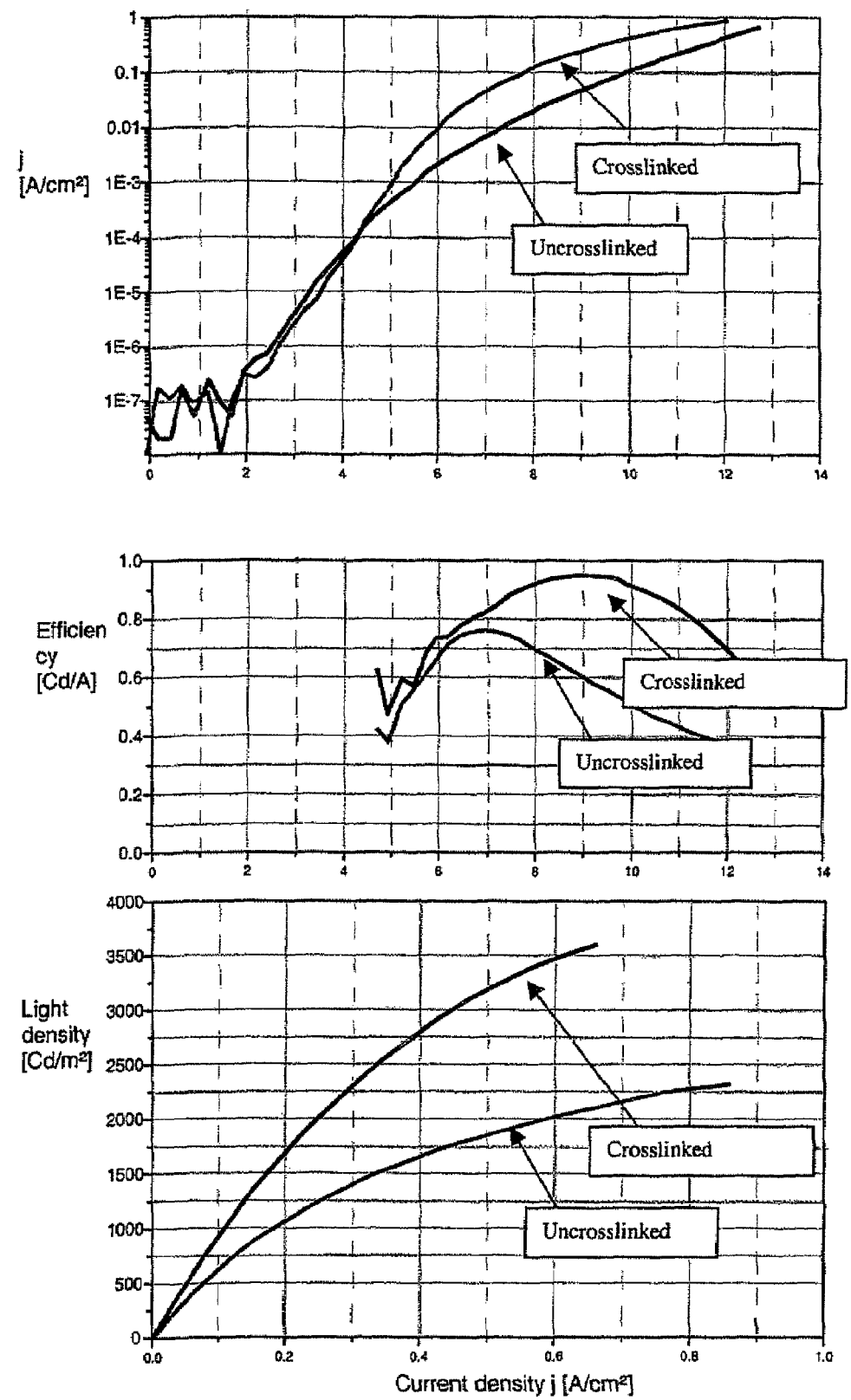
FIG. 1 illustrates the device data for crosslinked and uncrosslinked polymer P1 according to the invention.

The electronics materials according to the invention are electroluminescent or laser materials such as A) homo- or copolymers based on PPV or polyfluorenes or polyspiro
B) low molecular weight compounds having a 3-dimensional spirobifluorene structure,
C) low molecular weight compounds having a 3-dimensional triptycene structure
D) low molecular weight compounds having a 2-dimensional triphenylene structure
E) derivatives of perylenetetracarboxylic diimide
F) derivatives of quinaciridone
G) organic lanthanide complexes
H) derivatives of aluminum tris-quinoxalinate
I) oxadiazole derivatives or hole conductors such as J) polystyrenes, polyacrylates, polyamides or polyesters which bear derivatives of tetraarylbenzidine in the side chain,
K) low molecular weight compounds having a 2-dimensional triphenylene structure or electron conductors such as
L) derivatives of aluminum tris-quinoxalinate
M) oxadiazole derivatives.

The oxetane content is defined by the molar ratio of oxetane rings based on all organic rings, i.e. including the oxetane rings, in the particular structure. This can generally be determined by analytical methods. In addition to IR spectroscopy, one of the preferred methods is nuclear magnetic resonance spectroscopy (NMR).

For the purposes of the invention, rings are cyclic structural-elements formed from at least three ring atoms with the proviso that at least two carbon atoms are present (The Ring Index, Patterson and Capell, Reinhold Publishing Company, 1940 and Handbook of Chemistry and Physics, $62^{nd}$ ed. 1981, C-48).

The oxetane content may be varied within wide ranges of from 0.01 to 0.6. In the lower range, low degrees of crosslinking are achieved which result in relatively soft, rubber-elastic to gel-like layers. In the upper range, high crosslinking densities are achieved having thermoset-like properties, for example Bakelite.

A1) The homo- and copolymers of PPV contain one or more structural units of the formula (B), where at least one hydrogen atom in the polymer is replaced by a substituent of the formula (A).

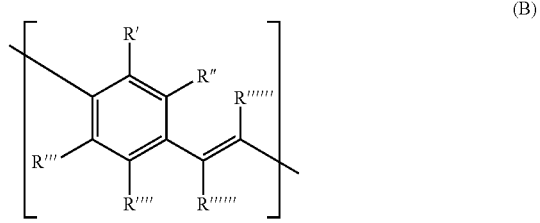

(B)

The substituents R' to R'''''' are the same or different and are each H, CN, F, Cl or a straight-chain, branched or cyclic alkyl or alkoxy group having from 1 to 20 carbon atoms where one or more nonadjacent $CH_2$ groups may be replaced by —O—, —S—, —CO—, —COO—, —O—CO—, —$NR^1$—, —$(NR^2R^3)^+$—$A^-$, or —$CONR^4$—, and where one or more hydrogen atoms may be replaced by F, or an aryl group having from 4 to 14 carbon atoms which may be substituted by one or more nonaromatic radicals R'.

$R_1, R_2, R_3, R_4$ are the same or different and are each aliphatic or aromatic hydrocarbon radicals having from 1 to 20 carbon atoms or else hydrogen.

$A^-$: is a singly charged anion or its equivalent.

Preference is given to PPVs according to WO 98/27136, which are represented in formula (C)

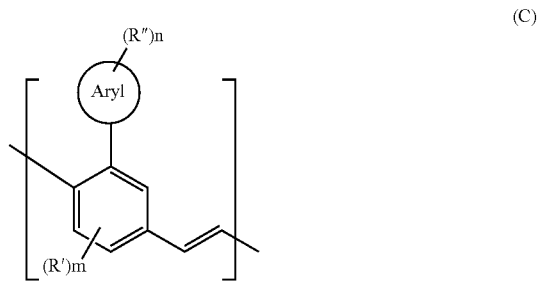

(C)

where the symbols and indices are defined as follows:

Aryl: is an aryl group having from 4 to 14 carbon atoms;

R', R'': are the same or different and are each a straight-chain or branched or cyclic alkyl or alkoxy group having from 1 to 20 carbon atoms where one or more nonadjacent $CH_2$ groups may be replaced by —O—, —S—, —CO—, —COO—, —O—CO—, —$NR^1$—, —$(NR^2R^3)^+$—$A^-$, or —$CONR^4$—, and where one or more hydrogen atoms may be replaced by F, or are CN, F, Cl or an aryl groups having from 4 to 14 carbon atoms which may be substituted by one or more nonaromatic radicals R';

$R^1, R^2, R^3, R^4$ are the same or different and are each aliphatic or aromatic hydrocarbon radicals having from 1 to 20 carbon atoms or else H.

$A^-$: is a singly charged anion or its equivalent;

m: is 0, 1 or 2;

n: is 1, 2, 3, 4 or 5.

Particular preference is given to polymers consisting mainly of repeating units of the formula (C).

Very particular preference is also given to copolymers consisting substantially of, more preferably consisting of, repeating units of the formula (I) and further repeating units which preferably likewise contain poly(arylenevinylene) structures, more preferably 2,5-dialkoxy-1,4-phenylenevinylene structures, where the alkoxy groups are preferably straight-chain or branched and contain from 1 to 22 carbon atoms.

For the purposes of the invention, copolymers comprise random, alternating, regular and also block structures.

Preference is likewise given to polymers containing repeating units of the formula (C) in which the symbols and indices are defined as follows:

Aryl is phenyl, 1- or 2-naphthyl, 1-, 2- or 9-anthracenyl, 2-, 3- or 4-pyridinyl, 2-, 4- or 5-pyrimidinyl, 2-pyrazinyl, 3- or 4-pyridazinyl, 2-, 3-, 4-, 5-, 6-, 7- or 8-quinoline, 2- or 3-thiophenyl, 2- or 3-pyrrolyl, 2- or 3-furanyl or 2-(1,3,4-oxadiazol)yl;

R' is in each case the same or different and is CN, F, Cl, $CF_3$ or a straight-chain or branched alkoxy group having from 1 to 12 carbon atoms;

R" is in each case the same or different and is a straight-chain or branched alkyl or alkoxy group having from 1 to 12 carbon atoms;

n is 0, 1, 2 or 3, more preferably 0, 1 or 2.

The preparation of such polymers is described in detail in WO 98/27136. Corresponding polymers according to the invention may be prepared by copolymerizing appropriate monomers which contain the oxetane group of the formula (A).

A2) The homo- and copolymers of polyfluorene contain one or more structural units of the formula (D), where at least one hydrogen atom in the polymer is replaced by a substituent of the formula (A).

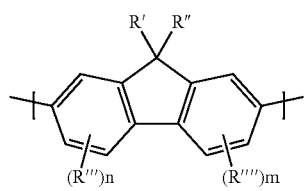

(D)

The substituents R' to R'''' are the same or different and are H, CN, F, Cl or a straight-chain, branched or cyclic alkyl or alkoxy group having from 1 to 20 carbon atoms where one or more nonadjacent $CH_2$ groups may be replaced by —O—, —S—, —CO—, —COO—, —O—CO—, —$NR^1$—, —($NR^2R^3$)$^+$—$A^-$, or —$CONR^4$—, and where one or more hydrogen atoms may be replaced by F, or an aryl group having from 4 to 14 carbon atoms which may be substituted by one or more nonaromatic radicals R'.

$R^1$, $R^2$, $R^3$, $R^4$ are the same or different and are each aliphatic or aromatic hydrocarbon radicals having from 1 to 20 carbon atoms or else hydrogen.

$A^-$: is a singly charged anion or its equivalent;

n, m: are each 0, 1, 2 or 3, preferably 0 or 1.

A2.1) Preference is given to structures according to DE-A-19846767 which are detailed hereinbelow. In addition to structural units of the formula (E1)

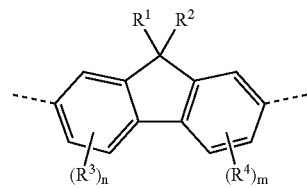

(E1)

where $R^1$, $R^2$ are the same or different and are each hydrogen, $C_1$-$C_{22}$-alkyl, $C_2$-$C_{20}$-heteroaryl, $C_5$-$C_{20}$-aryl, F, Cl or CN; where the abovementioned alkyl radicals may be branched or unbranched or else be cycloalkyls, and individual, nonadjacent $CH_2$ groups of the alkyl radical may be replaced by O, S, C=O, COO, N—$R^5$ or else $C_2$-$C_{10}$-aryls or heteroaryls, where the abovementioned aryls/heteroaryls may be substituted by one or more nonaromatic substituents $R^3$. Preference is given to compounds in which $R^1$ and $R^2$ are both the same and are not hydrogen or chlorine; preference is further given to compounds in which $R^1$ and $R^2$ are different and are also not hydrogen;

$R^3$, $R^4$ are the same or different and are each H, $C_1$-$C_{22}$-alkyl, $C_2$-$C_{20}$-heteroaryl, $C_5$-$C_{20}$-aryl, F, Cl, CN, $SO_3R^5$ or $NR^5R^6$; the alkyl radicals may be branched or unbranched or else be cycloalkyls; and individual, nonadjacent $CH_2$ groups of the alkyl radical may be replaced by O, S, C=O, COO, N—$R^5$ or $C_2$-$C_{10}$-aryls or heteroaryls, where the abovementioned aryls/heteroaryls may be substituted by one or more nonaromatic substituents $R^3$, $R^5$, $R^6$ are the same or different and are each hydrogen, $C_1$-$C_{22}$-alkyl, $C_2$-$C_{20}$-heteroaryl or $C_5$-$C_{20}$-aryl; the alkyl radicals may be branched or unbranched or else be cycloalkyls; and individual, nonadjacent $CH_2$ groups of the alkyl radical may be replaced by O, S, C=O, COO, N $R^5$ or else $C_2$ $C_{10}$ aryls, where the abovementioned aryls may be substituted by one or more nonaromatic substituents $R^3$, and m, n are each an integer 0, 1, 2 or 3, preferably 0 or 1, these polymers contain structural units of the formula (E2)

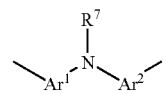

(E2)

where $Ar^1$, $Ar^2$ are each mono- or polycyclic aromatic conjugated systems having from 2 to 40 carbon atoms in which one or more carbon atoms may be replaced by nitrogen, oxygen or sulfur, and which may be substituted by one or more substituents $R^3$. It is entirely possible or sometimes even preferred that the aromatics $Ar^1$ and $Ar^2$ are bonded to each other via a bond or a further substituted or unsubstituted carbon atom or heteroatom and thus form a common ring.

$R^7$ is in each case the same or different and is $C_1$-$C_{22}$-alkyl, $C_2$-$C_{20}$-heteroaryls or $C_5$-$C_{20}$-aryl; the alkyl radicals may be branched or unbranched or else be cycloalkyls; and individual, nonadjacent $CH_2$ groups of the alkyl radical may be replaced by O, S, C=O, COO, N—$R^5$ or else simple aryls, where the abovementioned aryls/heteroaryls may be substituted by one or more nonaromatic substituents $R^3$.

Very particular preference is given to the structural units of the formula (E2) being derived from the following basic units:

diphenylamine derivatives which are incorporated into the polymer in the 4,4'-position;

phenothiazine or phenoxazine derivatives which are incorporated into the polymer in the 3,7-position;

carbazole derivatives which are incorporated into the polymer in the 3,6-position;

dihydrophenazine derivatives which are incorporated into the polymer in the 2,6- or 2,7-position;

dihydroaciridine derivatives which are incorporated into the polymer in the 3,7-position.

A2.2) Preference is likewise given to structures according to DE-A-19846766 which are detailed hereinbelow. These polymers contain structural units of the formula (F)

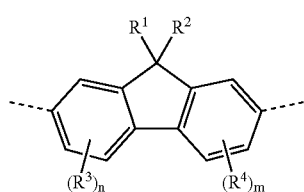

(F)

where $R^1$, $R^2$ are two different substituents from the group of $C_2$-$C_{40}$-aryl or heteroaryl; where the abovementioned aryls or heteroaryls may be substituted by one or more substituents $R^3$; for the purposes of this invention, the aryls and heteroaryls are of different types when they differ in the type or arrangement of substituents, $R^3$, $R^4$ are the same or different and are each $C_1$-$C_{22}$-alkyl, $C_2$-$C_{20}$-aryl, F, Cl, CN, $SO_3R^5$ or $NR^5R^6$; the alkyl radicals may be branched or unbranched or else be cycloalkyls; and individual, nonadjacent $CH_2$ groups of the alkyl radical may be replaced by O, S, C=O, COO, N—$R^5$ or else simple aryls, where the abovementioned aryls may be substituted by one or more nonaromatic substituents $R^3$, $R^5$, $R^6$ are the same or different and are each H, $C_1$-$C_{22}$-alkyl or $C_2$-$C_{20}$-aryl; the alkyl radicals may be branched or unbranched or else be cycloalkyls; and individual, nonadjacent $CH_2$ groups of the alkyl radical may be replaced by O, S, C=O, COO, N—$R^5$ or else simple aryls, where the abovementioned aryls may be substituted by one or more nonaromatic substituents $R^3$, and m, n are each an integer 0, 1, 2 or 3, preferably 0 or 1.

Very particular preference is given to $R^1$, $R^2$ being two different substituents from the group of $C_5$-$C_{40}$-aryl and $C_2$-$C_{40}$-heteroaryl; where the abovementioned aryls and heteroaryls may be substituted by one or more $R^3$ substituents.

A2.3) Preference is likewise given to structures according to DE 19846768.0 which are detailed hereinbelow. These are polyfluorenes which, in addition to units of the formula (E1)

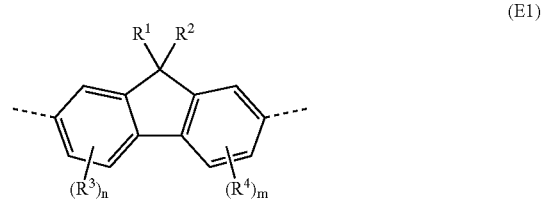

(E1)

where $R^1$, $R^2$ are the same or different and are each hydrogen, $C_1$-$C_{22}$-alkyl, $C_2$-$C_{20}$-aryl or -heteroaryl, F, Cl or CN; where the abovementioned alkyl radicals may be branched or unbranched or else be cycloalkyls, and individual, nonadjacent $CH_2$ groups of the alkyl radical may be replaced by O, S, C=O, COO, N—$R^5$ or else simple aryls, where the abovementioned aryls may be substituted by one or more substituents $R^3$. Preference is given to compounds in which $R^1$ and $R^2$ are both the same and are not hydrogen or chlorine; preference is further given to compounds in which $R^1$ and $R^2$ are different and are also not hydrogen;

$R^3$, $R^4$ are the same or different and are each, $C_1$-$C_{22}$-alkyl, $C_2$-$C_{20}$-aryl or -heteroaryl, F, Cl, CN, $SO_3R^5$ or $NR^5R^6$; the alkyl radicals may be branched or unbranched or else be cycloalkyls; and individual, nonadjacent $CH_2$ groups of the alkyl radical may be replaced by O, S, C=O, COO, N—$R^5$ or else simple aryls, where the abovementioned aryls may be substituted by one or more nonaromatic substituents $R^3$, $R^5$, $R^6$ are the same or different and are each hydrogen, $C_1$-$C_{22}$-alkyl, or $C_2$-$C_{20}$-aryl; the alkyl radicals may be branched or unbranched or else be cycloalkyls; and individual, nonadjacent $CH_2$ groups of the alkyl radical may be replaced by O, S, C=O, COO, N—$R^5$ or else simple aryls, where the abovementioned aryls may be substituted by one or more nonaromatic substituents $R^3$, and m, n are each an integer 0, 1, 2 or 3, preferably 0 or 1, always also contain structural units of the formula (G1)*

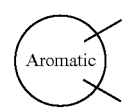

(G1)

where

Aromatic is a mono- or polycyclic aromatic conjugated system having from 5 to 20 carbon atoms in which one or more carbon atoms may be replaced by nitrogen, oxygen or sulfur, and whose linking points are chosen in such a way that an angle along the main polymer chain unequal to 180°, preferably less than 120°, particularly preferably less than 90° results.

In this context, particular preference is given to polymers containing at least 1 mol %, preferably from 2 mol % to 50 mol %, of structural units (one or more different) of the structural unit (G1).

The preparation of such polymers is described in detail in DE-A-19846767, DE-A-19846766 and DE-A-19846768. Corresponding polymers according to the invention may be prepared by copolymerizing corresponding monomers which bear the oxetane group.

A3) The homo- and copolymers of the polyspiro contain one or more structural units of the formula (H) where at least one hydrogen atom in the polymer are replaced by a substituent of the formula (A).

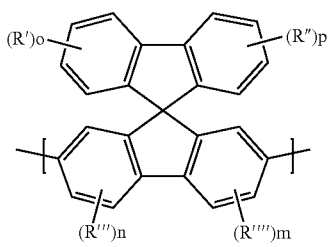

(H)

The substituents R' to R'''' are the same or different and are H, CN, F, Cl or a straight-chain, branched or cyclic alkyl or alkoxy group having from 1 to 20 carbon atoms where one or more nonadjacent CH$_2$ groups may be replaced by —O—, —S—, —CO—, —COO—, —O—CO—, —NR$^1$—, —(NR$^2$R$^3$)$^+$—A$^-$, or —CONR$^4$—, and where one or more hydrogen atoms may be replaced by F, or an aryl group having from 4 to 40 carbon atoms which may be substituted by one or more nonaromatic radicals R'.

R$^1$, R$^2$, R$^3$, R$^4$ are the same or different and are each aliphatic or aromatic hydrocarbon radicals having from 1 to 20 carbon atoms or else hydrogen.

A$^-$: is a singly charged anion or its equivalent;

n, m, o, p: are each 0, 1, 2 or 3, preferably 0, 1 or 2.

Preferred embodiments of the polyspiros are contained in (U.S. Pat. No. 5,621,131).

The preparation of such polymers is described in detail in U.S. Pat. No. 5,621,131. Corresponding polymers according to the invention may be prepared by copolymerizing appropriate monomers which bear the oxetane group.

B) The low molecular weight compounds having a 3-dimensional spirobifluorene structure consist of structural units of the formula (I1)

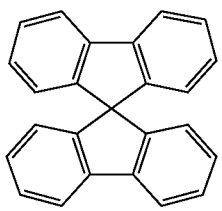

(I1)

where the benzo groups may each independently be substituted and/or fused and where at least one hydrogen atom is replaced by a substituent of the formula (A). In this context, preference is given to using compounds according to EP-A-0676461, as represented in formula (I2)

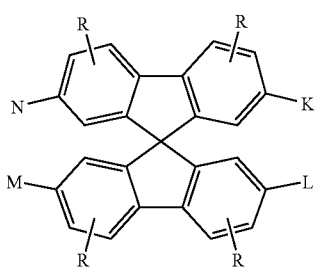

(I2)

where the symbols and indices are defined as follows:

K, L, M, N are the same or different and are each

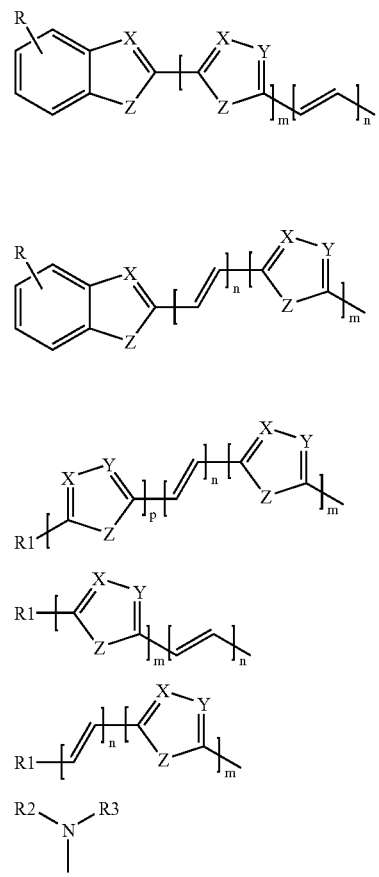

R may in each case be the same or different and have the same definition as K, L, M or N, or is H, a linear or branched alkyl, alkoxy or ester group having from 1 to 22 carbon atoms, —CN, —NO$_2$, —NR$^2$R$^3$, —Ar or —O—Ar;

Ar is phenyl, biphenyl, 1-naphthyl, 2-naphthyl, 2-thienyl or 2-furanyl, where each of these groups may bear one or two R radicals, m, n, p, are each 0, 1, 2 or 3;

X, Y are the same or different and are CR, N;

Z is —O—, —S—, —NR$^1$—, —CR$^1$R$^4$—, —CH=CH— or —CH=N—;

R$^1$, R$^4$ may be the same or different and may each have the same definition as R R$^2$, R$^3$ are the same or different and are each H, a linear or branched alkyl group having from 1 to 22 carbon atoms, —Ar or 3-methylphenyl.

The preparation of such compounds is described in detail in EP 676461. Corresponding compounds according to the invention can be prepared by replacing appropriate substituents or hydrogen atoms by the oxetane group of the formula (A).

C) The low molecular weight compounds having a 3-dimensional triptycene structure consist of structural units of the formula (J)

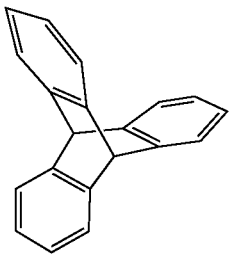

(J)

where the benzo groups may each independently be substituted and/or fused and where at least one hydrogen atom is replaced by a substituent of the formula (A). Preference is given to using compounds according to DE-A-19744792. The preparation of such compounds is described in detail in DE-A-19744792. Corresponding compounds according to the invention can be prepared by replacing appropriate substituents or hydrogen atoms by the oxetane group of the formula (A).

D) The low molecular weight compounds having a 2-dimensional triphenylene structure consist of structural units of the formula (K)

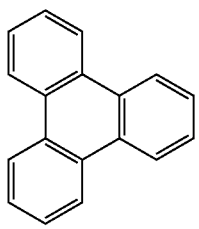

(K)

where the benzo groups may each independently be substituted and/or fused and where at least one hydrogen atom is replaced by a substituent of the formula (A). Preference is given to using compounds according to DE-A-4422332. The preparation of such compounds is described in detail in DE-A-4422332. Corresponding compounds according to the invention can be prepared by replacing appropriate substituents or hydrogen atoms by the oxetane group of the formula (A).

E) The derivatives of the perylenetetracarboxylic diimide consist of structural units of the formula (L)

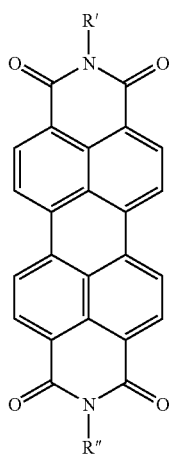

(L)

where the benzo groups may each independently be substituted and where at least one hydrogen atom is replaced by a substituent of the formula (A). Similarly to R' and R", these substituents may be the same or different and may each be a straight-chain, branched or cyclic alkyl or alkoxy group having from 1 to 20 carbon atoms where one or more nonadjacent $CH_2$ groups may be replaced by —O—, —S—, —CO—, —COO—, —O—CO—, —$NR^1$—, —$(NR^2R^3)^+$—$A^-$, or —$CONR^4$—, and where one or more hydrogen atoms may be replaced by F, or an aryl group having from 4 to 14 carbon atoms which may be substituted by one or more nonaromatic radicals R'. Furthermore, the substituents other than R' and R" may also be CN, F or Cl.

Corresponding compounds according to the invention can be prepared by replacing appropriate substituents or hydrogen atoms with the oxetane group of the formula (A).

F) The derivatives of quinaciridone consist of structural units of the formula (M)

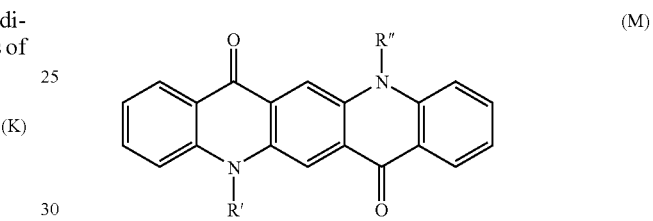

(M)

where the benzo groups may each independently be substituted and where at least one hydrogen atom is replaced by a substituent of the formula (A).

Similarly to R' and R", these substituents may be the same or different and may each be a straight-chain, branched or cyclic alkyl or alkoxy group having from 1 to 20 carbon atoms where one or more nonadjacent $CH_2$ groups may be replaced by —O—, —S—, —CO—, —COO—, —O—CO—, —$NR^1$—, —$(NR^2R^3)^+$—$A^-$, or —$CONR^4$—, and where one or more hydrogen atoms may be replaced by F, or an aryl group having from 4 to 14 carbon atoms which may be substituted by one or more nonaromatic radicals R'. Furthermore, the substituents other than R' and R" may also be CN, F or Cl.

Corresponding compounds according to the invention can be prepared by replacing appropriate substituents or hydrogen atoms with the oxetane group of the formula (A).

G) The organic lanthanide complexes consist of structural units of the formula (N)

$$LnR'_n \qquad (N)$$

The substituents R' may be the same or different and each be carboxylates, ketonates, 1,3-diketonates, imides, amides or alkoxides, where at least one hydrogen atom is replaced by a substituent of the formula (A).

The number of ligands depends on the particular metal. Preference is given to the organic complexes of europium, gadolinium and terbium, particular preference to those of europium.

Corresponding compounds according to the invention can be prepared by replacing appropriate substituents or hydrogen atoms in the substituents by the oxetane group of the formula (A).

H) The derivatives of metal quinoxalinate consist of structural units of the formula (O)

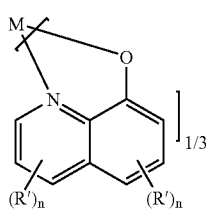

where the benzo groups may each independently be substituted by radicals R', M is aluminum, zinc, gallium or indium, preferably aluminum; n is an integer 0, 1, 2 or 3.

The substituents of the benzo group R' may be the same or different and may each be a straight-chain, branched or cyclic alkyl or alkoxy group having from 1 to 20 carbon atoms where one or more nonadjacent $CH_2$ groups may be replaced by —O—, —S—, —CO—, —COO—, —O—CO—, —NR$^1$—, —(NR$^2$R$^3$)$^+$—A$^-$, or —CONR$^4$—, and where one or more hydrogen atoms may be replaced by F, or an aryl group having from 4 to 14 carbon atoms which may be substituted by one or more nonaromatic radicals R'. Furthermore, the substituents other than R' and R" may also be CN, F or Cl. The oxetane group according to the invention of the formula (A) may then either replace a hydrogen atom on one of the quinoxaline rings, or else be on another ligand R' which replaces one of the quinoxaline ligands.

I) The derivatives of oxadiazole consist of structural units of the formula (P)

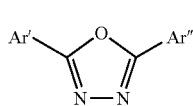

where Ar' and Ar" may be the same or different and each be a substituted or unsubstituted aromatic or heteroaromatic having from 4 to 14 carbon atoms, where at least one hydrogen atom is replaced by a substituent of the formula (A).

Preference is given to Ar' and Ar" being the same or different and each being phenyl, 1- or 2-naphthyl, 1-, 2- or 9-anthracenyl, 2-, 3- or 4-pyridinyl, 2-, 4- or 5-pyrimidinyl, 2-pyrazinyl, 3- or 4-pyridazinyl, 2-, 3-, 4-, 5-, 6-, 7- or 8-quinoline, 2- or 3-thiophenyl, 2- or 3-pyrrolyl, 2- or 3-furanyl.

The possible substituents are the same or different and are each CN, F, Cl, $CF_3$ or a straight-chain, cyclic or branched alkyl or alkoxy group having from 1 to 12 carbon atoms, where one or more nonadjacent $CH_2$ groups may be replaced by —O—, —S—, —CO—, —COO—, —O—CO—, —NR$^1$—, —(NR$^2$R$^3$)$^+$—A$^-$, or —CONR$^4$—, and where one or more hydrogen atoms may be replaced by F.

The oxetane group according to the invention of the formula (A) may then either replace a hydrogen atom on one of the aryl rings, or else be on one of the substituents of the aryl rings.

J) Polymers (polystyrenes which bear tetraarylbenzidine units in the side chain consist of structural units of the formula (Q) or analogous compounds in other basic polymer frameworks (polyacrylates, polyamides, polyesters)

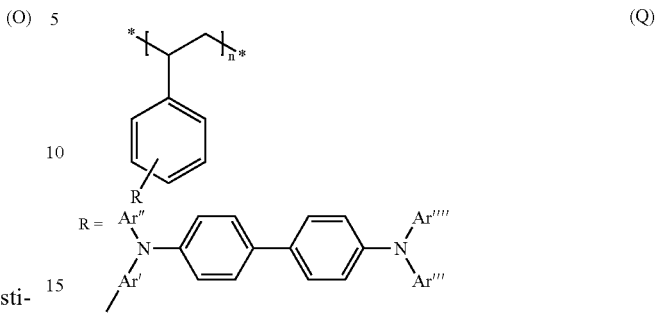

where Ar', Ar", Ar''' and Ar'''' may be the same or different and may each be a substituted or unsubstituted aromatic or heteroaromatic having from 4 to 14 carbon atoms.

Preference is given to Ar', Ar", Ar''' and Ar'''' being the same or different and each being phenyl, 1- or 2-naphthyl, 1-, 2- or 9-anthracenyl, 2-, 3- or 4-pyridinyl, 2-, 4- or 5-pyrimidinyl, 2-pyrazinyl, 3- or 4-pyridazinyl, 2-, 3-, 4-, 5-, 6-, 7- or 8-quinoline, 2- or 3-thiophenyl, 2- or 3-pyrrolyl, 2- or 3-furanyl.

The possible substituents are the same or different and are each CN, F, Cl, $CF_3$ or a straight-chain, cyclic or branched alkyl or alkoxy group having from 1 to 12 carbon atoms, where one or more nonadjacent $CH_2$ groups may be replaced by —O—, —S—, —CO—, —COO—, —O—CO—, —NR$^1$—, —(NR$^2$R$^3$)$^+$—A$^-$, or —CONR$^4$—, and where one or more hydrogen atoms may be replaced by F.

This tetraarylbenzidine group is then bonded to the main polymer chain via a spacer, preferably a $C_1$ to $C_6$ alkyl, alkoxy or ester group.

The oxetane group according to the invention of the formula (A) may then either replace a hydrogen atom on one of the aryl rings, or be on one of the substituents of the aryl rings, or else on a further copolymerized monomer which bears no tetraarylbenzidine unit.

The above-outlined substances may be used in pure form or else in a mixture with each other or with other auxiliaries.

The invention further provides mixtures or formulation comprising the materials according to the invention and added auxiliaries, such as initiators and optionally sensitizers, stabilizers, retarders, inhibitors, reactive diluents, etc.

At least one photoinitiator or a photoinitiator system is added to the materials according to the invention. The concentration is typically chosen within the range from 0.1 to 1.0% by weight, based on the compound/polymer according to the invention. Irradiation with actinic radiation generates an acid which initiates a crosslinking reaction by cationic, ring-opening polymerization.

Structured irradiation allows a pattern of regions having crosslinked material and regions having uncrosslinked material to be obtained. Suitable operations (for example washing with suitable solvents) then allows the regions having uncrosslinked material to be removed. This leads to the desired structuring.

When the crosslinking of relatively large areas is desired, crosslinking may be initiated after film formation by applying an acid.

A further advantageous effect according to the invention is that the crosslinking increases the mechanical and thermal stability of the layers generated with the materials according to the invention. This leads to the devices which comprise crosslinked materials according to the invention having distinctly longer lives under corresponding conditions (for example thermal stress, mechanical stress). This effect is more marked the greater the degree of crosslinking.

This completes the subsequent application of the different layers after completed crosslinking. For example, an already crosslinked layer may be effected as a substrate for depositing further substances from the liquid phase. When the materials having different optical refractive indices are selected in a targeted manner, the layer construction obtained in this way may be used as a waveguide. Preference is given to applying the emitter from the solution to an already crosslinked layer of a hole conductor or electron conductor. With the aid of the materials according to the invention, it is possible to produce multilayer devices using soluble active materials.

The structuring is effected, as described above, by irradiation. This is a standard process in the present-day electronics industry and may be effected, for example, by irradiating with lasers or by surface irradiation through an appropriate mask. In contrast to the above-outlined mask with disadvantages, this mask harbors no risk of deposition, since there is in this case only radiation and no material flow through the mask.

In the case of the laser as the source, lateral positioning is possible either by moving the substrate, the light source itself or by optical aids. A possible aid for substrate movement is an XY-table which is driven by stepping motors. Optical aids may be mirrors. Structuring is particularly simple and rapid where a shadow mask is used which is irradiated with a surface light source, for example a very high pressure Hg lamp.

The invention further provides the layers which result from crosslinking.

The invention therefore likewise provides a structured organic electronic device which, for the purposes of this invention, has one or more active layers, at least one of which has been produced from one or more materials according to the invention of the formula (A).

The general construction of such devices has been described above, and is listed in detail here once again:
(i) OLEDs and PLEDs in analogy with EP 676 461 and WO 98-27136 and the literature cited therein.
(ii) Organic solar cells in analogy with WO 94-05045 and WO 98-48433 and the literature cited therein.
(iii) Organic lasers in analogy with WO 98-03566 and the literature cited therein.
(iv) Organic circuits (ICs) in analogy with WO 95-31833 and WO 99-10939 and the literature cited therein.

The invention is further illustrated by the examples which follow, without wishing to restrict it.

Part A: Synthesis of the Monomers: Monomers for Units of the Formula (D) (Fluorenes)

Example M1

Preparation of 9-(2,5-dimethylphenyl)-9-(4-oxymethylene{2-[(3-ethylyloxetane)-3-yl)}phenyl)-2,7-dibromofluorene (M1)

In a 50 ml four-neck flask, 808 mg (6 mmol) of 2-ethyl-2-chloromethyloxetane (see Chemphyschem. 2000, 207), 345 mg (5.2 mmol) of KOH (85%), 2.60 g (5 mmol) of 9-(2,5-dimethylphenyl)-9-(4-hydroxyphenyl)-2,7-dibromofluorene (see WO 00/22026) were cautiously admixed with KOH and heated to 150° C. A further three portions, each of 808 mg (each 6 mmol), of 2-ethyl-2-chloromethyloxetane were then added over the course of two hours and the mixture was stirred at this temperature for a further 2 hours. The reaction was followed by TLC (hexane/CHCl$_3$ 1:1). The reaction mixture was cooled and admixed at room temperature with 50 ml of water. The mixture was then admixed with ethyl acetate (50 ml). A white solid precipitated which dissolved neither in the aqueous nor in the organic phase. It was filtered off with suction. After drying under reduced pressure, 2.2 g (3.55 mmol, 71%) of the monomer M1, which, according to $^1$H NMR, was >99% pure, were obtained. $^1$H NMR (benzene-d$_6$, 400 MHz): 7.72 (dd, 2H, J=2.0, 0.8, fluorene H1/H8); 7.28 (dd, 2H, J=2.0, 7.8, fluorene H3/H6); 7.21 (br. s, 1H, H-6" phenyl); 7.06 (d with fine structure, 4H, J=8.0 Hz, H-phenyl); 6.88-6.80 (m, 2H, H3", H4"); 6.47 (d with fine structure, 2H, j, 7.7 Hz, fluorene H4/H5), 4.35 (d, J=7.2 Hz, 2H oxetane); 4.25 (d, J=7.0 Hz, 2H-oxetane); 3.55 (s, 2H, OCH$_2$); 2.01 (s, 3H, CH$_3$); 1.55 (q, 2H, J=6.8 Hz, CH$_2$-ethyl); including at 1.54 (s, 3H, CH$_3$); 0.61 (t, J=6.8 Hz, CH$_3$-ethyl).

Example M2

Preparation of 9-(2,5-dimethylphenyl)-9-{6-[(3-methyloxetane)-3-yl)methoxy]-hexoxy}-2,7-dibromofluorene (Monomer M2)

In a similar manner to Example M1, 2.22 g (5 mmol) of 9-(2,5-dimethylphenyl)-9-hydroxy-2,7-dibromofluorene (see WO 00/22026) were reacted with 2.65 g (2 eq) of (6'-bromohexyloxy-3-methyl)-3-methyloxetane (see Polym. J. 1993; 25, 1283) at 50° C. for 23 h. 2.04 g (3.25 mmol, 65%) of the monomer M2 were obtained which, according to $^1$H NMR, was of >98% purity.

$^1$H NMR (CDCl$_3$, 400 MHz): 7.50 2 (br. s, 7H, fluorene-H, H6); 7.06 (d, 1H, J=8.0 Hz, H-3'); 6.88 (d, 1H, J=8.0 Hz, H-4'); 4.38 (d, J=7.2 Hz, 2H oxetane); 4.22 (d, J=7.0 Hz, 2H oxetane); 3.63 (m, 4H, OCH$_2$); 2.88 (s, 2H, OCH$_2$); 2.31 (s, 3H, CH$_3$); 1.78-1.20 (m, 14H, 4×CH$_2$, 2×CH$_3$).

Example M3

Preparation of 9,9-bis{6-[(3-methyloxetane)-3-yl) methoxy]-hexoxy}-2,7-dibromofluorene (M3)

In a 250 mL one-neck flask equipped with a reflux condenser, 1.44 g (60 mmol) of NaH were suspended in 50 mL of dry toluene and 50 mL of dry DMA. 3.24 g (10 mmol) of 2,7-dibromofluorene and 5.57 g (21 mmol) of (6'-bromohexyloxy-3-methyl)-3-methyloxetane were added to this reaction mixture and heated to 100° C. for 1 h. After cooling to room temperature, 1 mL of H$_2$O was cautiously added by pipette and then 150 mL of Et$_2$O were added. The organic phase was washed with 4×50 mL of H$_2$O, then dried over MgSO$_4$ and the solvents were removed in vacuo. The pure product was obtained by column chromatography (twice) on silica gel using an eluent mixture of ethyl acetate:petroleum ether=1:2. Yield: 3.78 g (39%) of viscous oil.

$^1$H NMR (CDCl$_3$, 300 MHz): 0.65 (m, 4H), 1.09 (m, 4H), 1.27 (s, 6H), 1.40 (m, 4H), 1.89 (m, 4H), 3.34 (t, J=6.6 Hz, 4H), 3.40 (s, 4H), 4.31-4.47 (AA'BB' system, J=5.7 Hz, 8H), 7.43-7.51 (AA'BB' system, J=8.1 Hz, 4H), 7.43 (m, 2H). $^{13}$C NMR (CDCl3, 75 MHz): δ=21.4 (CH3), 24.0 (CH2), 26.1 (CH2), 29.8 (CH2), 30.0 (CH2), 40.3 (C$_{quart}$) 40.5 (CH2), 56.0 (C$_{quart}$), 71.9 (CH$_2$), 76.4 (CH$_2$), 80.6 (CH$_2$), 121.6 (CH), 121.9 (CH), 126.5 (CH), 130.6 (C$_{quart}$), 139.5 (C$_{quart}$), 152.8 (C$_{quart}$). MS (70 eV, 70 eV, m/z (%)): 692 (M+, 100), 690 (50), 662 (12), 614 (12), 612(11), 349 (14), 323 (30), 245 (10), 243 (10), 85 (38), 55 (23). IR (film, KBr):=3048 cm$^{-1}$, 2931, 2860, 2797, 1598, 1570, 1450, 1416, 1398, 1378, 1264, 1117, 1061, 1004, 979, 940, 878, 835, 811, 741 666, 427. UV/vis (CHCl$_3$) $\lambda_{max}$ ($\epsilon$)=282 nm (26178), 303 nm (14170), 314 nm (10110). C$_{35}$H$_{48}$Br$_2$O$_4$ (092.58): calc., C, 80.70; H, 8.99; Br, 23.07. found: C, 61.24; H, 6.83; Br, 22.77.

Example M4

Preparation of Monomer M4 (see Scheme 1)

M4 was prepared in a similar manner to M1 using 2.2 eq of (6'-bromohexyloxy-3-methyl)-3-methyloxetane. After a similar workup, 56% of M4 were obtained as a colorless solid.

The structures of the monomers according to the invention M1-M4 used and of further monomers are summarized in Scheme 1:

Scheme 1:
The preparation of the monomers not according to the invention M5–M11 is described in the unpublished application DE 10114477.6.

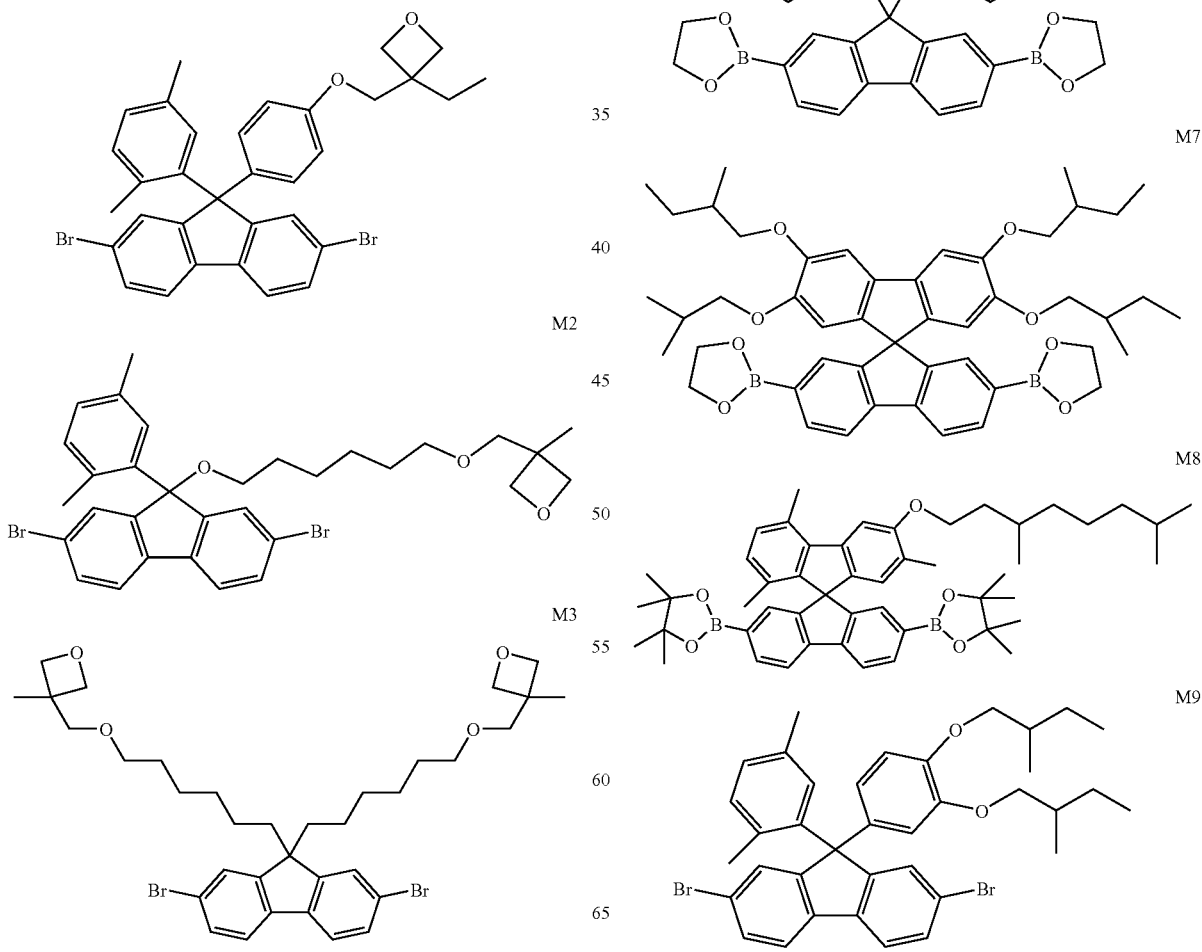

-continued

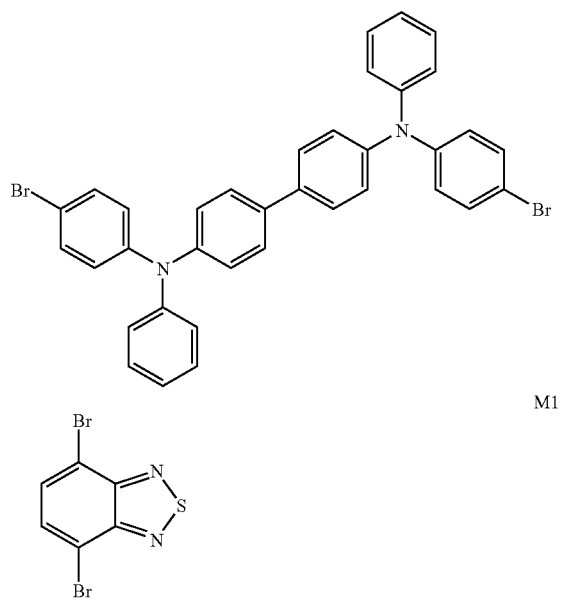

Part B: Preparation of the Polymers

Example P1

Copolymerization of monomer M1, 2,7-dibromo-9-(2',5'-dimethyl-phenyl)-9-[3'',4''-bis(2-methylbutyloxy)phenyl]fluorene (M9), N,N'-bis(4-bromo-phenyl)-N,N'-bisphenyl-benzidine (M10) and pinacolyl 9-(3,7-dimethyloctyloxyphenyl)-9-(2,5-dimethylphenyl)fluorene-2,7-bisborate (M8) by Suzuki reaction (polymer P1). 1.6237 g (2.400 mmol) of 2,7-dibromo-9-(2',5'-dimethyl-phenyl)-9-[3'',4''-bis(2-methylbutyloxy)phenyl]fluorene (M9), 4.5281 g (6.00 mmol) of pinacolyl 9-(3,7-dimethyloctyloxyphenyl)-9-(2,5-dimethylphenyl)fluorene-2,7-bisborate (M8), 0.7757 g (1.200 mmol) of N,N'-bis(4-bromophenyl)-N,N'-bis(phenyl)benzidine (M10), 1.4842 g (2.400 mmol) of monomer M1, 5.80 g (25.2 mmol) of $K_3PO_4 \cdot H_2O$, 18 ml of toluene, 9 ml of water and 0.15 ml of ethanol were degassed by passing $N_2$ through for 30 min. 57 mg (0.05 mmol) of $Pd(PPh_3)_4$ were then added under protective gas. The suspension was stirred vigorously under an $N_2$ blanket at an internal temperature of 87° C. (gentle reflux). After 4 days, a further 0.10 g of pinacoyl 9-(3,7-dimethyloctyloxyphenyl)-9-(2,5-dimethylphenyl)fluorene-2,7-bisborate was added. After heating for a further 6 hours, 0.3 ml of bromobenzene was added and heated was continued to a reflux for a further 3 h.

The reaction solution was diluted with 200 ml of toluene, and the solution was extracted by stirring with 200 ml of 2% aqueous NaCN for 3 h. The mixture lightened almost completely. The organic phase was washed with $H_2O$ and precipitated by adding to 800 ml of ethanol. The polymer was dissolved in 200 ml of chloroform at 40° C. for 1 h, filtered through Celite and precipitated with 250 ml of MeOH, washed and dried under reduced pressure. Precipitation was effected once more in 200 ml of THF/250 ml of methanol, followed by filtration with suction and drying to constant mass. 4.80 g (9.64 mmol, 80%) of the polymer P1 were obtained as a slightly yellow solid.

$^1H$ NMR ($CDCl_3$): 7.9-6.6 (m, fluorene-H, phenyl-H); 4.52 and 4.43 (2×d, J~8 Hz, each 0.4H, oxetane H); 4.0-3.4 (3×m, $OCH_2$), 2.20 (s, $CH_2$-ethyl, arom-$CH_3$); 1.9-0.7 (m, alkyl H).

GPC: THF; 1 ml/min, PLgel 10 μm Mixed-B 2×300×7.5 $mm^2$, 35° C., RI detection: Mw=77000 g/mol, Mn=32000 g/mol.

Further polymers were prepared in a similar manner to the descriptions for P1. The chemical properties are summarized in the table which follows. Some comparative polymers without oxetane units were also prepared. These are also listed in the table. All of these polymers were also investigated for use in PLEDs. The preparation of PLEDs is firstly detailed above and is described in more detail in Part C. The most important device properties (color, efficiency) are also listed in the table. In the case of the polymers P1-P9, the chemical and electrooptical data of the uncrosslinked polymers are shown. The crosslinking is likewise described in Part C.

TABLE 1

Important characteristic data of the polymers investigated

| Polymer | Proportion of the monomers in the polymerization [%] | | | | GPC* | | Electroluminescence** | | |
|---|---|---|---|---|---|---|---|---|---|
| | | | | | $M_W$ (·1000) | $M_N$ (·1000) | $\lambda_{max}$ | Max. Eff. | Voltage at 100 Cd/m² |
| (type)* | Monom. 1 | Monom. 2 | Monom. 3 | Monom. 4 | g/mol | g/mol | [nm] | [Cd/A] | [V] |
| P1 | 20% M1 | 20% M9 | 10% M10 | 50% M8 | 77 | 32 | 468 | 1.1 | 7.5 |
| P2 | 25% M2 | 25% M5 | 50% M6 | | 56 | 29 | 476 | 1.0 | 7.9 |
| P3 | 25% M3 | 25% M5 | 50% M6 | | 43 | 18 | 478 | 1.2 | 7.2 |
| P4 | 25% M4 | 25% M5 | 50% M6 | | 65 | 33 | 476 | 1.1 | 7.0 |
| P5 | 25% M4 | 15% M9 | 10% M10 | 50% M7 | 124 | 51 | 468 | 2.1 | 5.5 |
| P6 | 25% M2 | 15% M9 | 10% M10 | 50% M7 | 134 | 54 | 466 | 2.2 | 5.4 |
| P7 | 50% M1 | 50% M6 | | | 79 | 38 | 477 | 1.0 | 7.1 |
| P8 | 50% M4 | 40% M7 | 10% M9 | | 73 | 34 | 467 | 1.9 | 5.3 |
| P9 | 30% M2 | 10% M11 | 10% M10 | 50% M8 | 81 | 38 | 550 | 6.5 | 4.9 |
| C1 | 40% M9 | 10% M10 | 50% M8 | | 79 | 33 | 469 | 1.1 | 7.8 |
| C2 | 50% M5 | 50% M6 | | | 49 | 22 | 478 | 0.9 | 8.2 |
| C3 | 40% M9 | 10% M10 | 50% M7 | | 141 | 65 | 466 | 2.2 | 5.3 |

*GPC measurements THF; 1 ml/min, Plgel 10 μm Mixed-B 2 × 300 × 7.5 mm², 35° C., RI detection was calibrated against polystyrene
**For production of the polymer LEDs, see Part C Part C: Production and Characterization of LEDs, Crosslinking of the Polymers According to the Invention The LEDs were produced by the general procedure outlined hereinbelow. This of course had to be adapted ad hoc to the particular circumstances (for example polymer viscosity and optimal layer thickness of the polymer in the device). The LEDs described hereinbelow were each two-layer systems, i.e. substrate//ITO//PEDOT//polymer//cathode.

PEDOT is a polythiophene derivative.

General Procedure for Producing High-Efficiency, Long-Life LEDs:

Once the ITO-coated substrates (for example glass support, PET film) have been cut to the correct size, they are cleaned in a plurality of cleaning steps in an ultrasound bath (for example soap solution, Millipore water, isopropanol).

For drying, they are blown with an $N_2$ gun and stored in a desiccator. Before coating with the polymer, they are treated with an ozone plasma unit for approx. 20 minutes. A solution of the respective polymer (generally having a concentration of 4-25 mg/ml in, for example, toluene, chlorobenzene, xylene:cyclohexanone (4:1)) is prepared and dissolved by stirring at room temperature. Depending on the polymer, it may also be advantageous to stir at 50-70° C. for some time. When the polymer has dissolved completely, it is filtered through a 5 µm filter and coated using a spin coater at variable speeds (400-6000). This allows the layer thicknesses to be varied within the range from approx. 50 to 300 nm. A conductive polymer, preferably doped PEDOT or PANI, is usually applied initially to the (structured) ITO.

Electrodes are also applied to the polymer films. This is generally effected by thermal evaporation (Balzer BA360 or Pfeiffer PL S 500). The transparent ITO electrode is then connected as the anode and the metal electrode (for example Ba, Yb, Ca) as the cathode, and the device parameters are determined.

The results obtained with the polymers described are summarized in the table in Part B.

Crosslinking

The crosslinking of the polymers according to the invention was achieved by the following procedure:

The polymers were admixed in toluene solution (1.5%) with 3% by weight (based on the polymer) of photoacid (4-(thiophenoxyphenyl)diphenylsulfonium hexafluoro-antimonate) and spin coated under $N_2$ as described above. After drying the film, crosslinking was effected by irradiation using a UV lamp (10 W, 302 nm, 5 min). The film was then heat treated at 200° C. for 3 minutes under $N_2$ (Example P1, 130° C. for Examples P2-P9) and then treated with a $10^{-4}$ molar $LiAlH_4$ solution in THF. The device data for crosslinked and uncrosslinked polymer P1 are illustrated in FIG. 1. The values shown there were not obtained under optimized conditions (cathode/device structure), so that the absolute values of the efficiencies are lower than in Table 1.

Proof of Crosslinkability and Photostructurability

Figure 2:
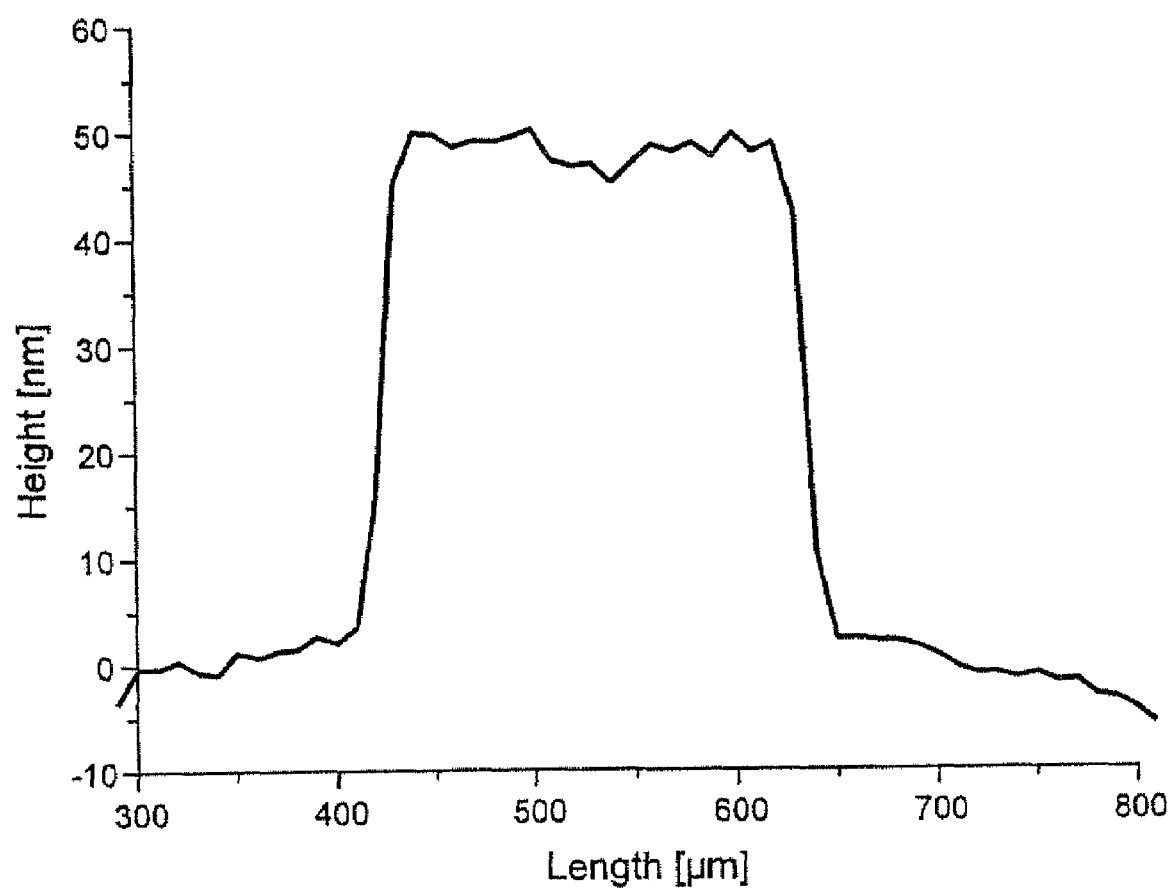
FIG. 2 illustrates the profile obtained using a profilmeter.

A thin film of thickness 50 nm was produced from the polymer P5 admixed with photoacid (see above) and illuminated through a comb structure having 200 µm teeth for 20 sec. The film was heated at 120° C. for 20 seconds and the soluble part was then washed off with THF. The profile obtained using a profilometer (FIG. 2) shows good agreement with the illuminated structure.

What is claimed is:

1. A low molecular weight or polymeric organic electroluminescent or laser material for use in electronic applications selected from the group consisting of A) a homo- or copolymer based on polyspiro, B) a low molecular weight compound having a 3-dimensional spirobifluorene structure, C) a low molecular weight compound having a 3-dimensional triptycene structure, and D) a derivative of quinacridone having at least one hydrogen atom, wherein at least one hydrogen atom is replaced by a group of the formula (A)

wherein

R is a straight-chain, branched or cyclic alkyl, alkoxyalkyl, alkoxy, thioalkoxy group having from 1 to 20 carbon atoms, $C_4$-$C_{18}$-aryl or $C_2$-$C_{10}$-alkenyl, in each of which one or more hydrogen atoms is optionally replaced by halogen or CN, and one or more nonadjacent carbon atoms is optionally replaced by —O—, —S—, —CO—, —COO— or —O—CO—, Z is —O—, —S—, —CO—, —COO—, —O—CO— or a bivalent group —$(CR_1R_2)_n$— in which $R_1$ and $R_2$ are each independently hydrogen, a straight-chain, branched or cyclic alkyl, alkoxy, alkoxyalkyl, thioalkoxy group having from 1 to 20 carbon atoms, $C_4$-$C_{18}$-aryl or $C_2$-$C_{10}$-alkenyl, in each of which one or more hydrogen atoms is optionally replaced by halogen or CN, and one or more nonadjacent carbon atoms is optionally replaced by —O—, —S—, —CO—, —COO— or —O—CO—, X is —O— or a bivalent group —$(CR_1R_2)_n$— in which $R_1$ and $R_2$ are each independently hydrogen, a straight-chain, branched or cyclic alkyl, alkoxy, alkoxyalkyl, thioalkoxy group having from 1 to 20 carbon atoms, $C_4$-$C_{13}$-aryl or $C_2$-$C_{10}$-alkenyl, in each of which one or more hydrogen atoms is optionally replaced by halogen or CN, and n is an integer from 1 to 20, with the proviso that the number of these A groups is limited by the maximum number of available substitutable hydrogen atoms.

2. The material as claimed in claim 1, wherein said halogen in the definition of R, X and Z is Cl or F and n is an integer from 3 to 10.

3. The material as claimed in claim 2, wherein n is an integer from 3 to 6.

4. The material as claimed in claim 1, wherein the content of oxetane group according to formula (A) by the molar ratio of oxetane rings, based on all organic rings including the oxetane rings in the particular structure, is from 0.01 to 0.6.

5. A low molecular weight or polymeric organic electroluminescent or laser material for use in electronic applications selected from the group consisting of A) a homo- or copolymer based on poly(p-phenylene-vinylene) ("PPV") or polyspiro, B) a low molecular weight compound having a 3-dimensional spirobifluorene structure, C) a low molecular weight compound having a 3-dimensional triptycene structure, and
D) a derivative of quinacridone
wherein each material contains at least one cross-linking enabled oxetane group.

6. The material as claimed in claim 5, wherein the content of oxetane group by the molar ratio of oxetane rings, based on all organic rings including the oxetane rings in the particular structure, is from 0.01 to 0.6.

7. The material as claimed in claim 1, wherein
X is —O— or a bivalent group —$(CR_1R_2)_n$— in which $R_1$ and $R_2$ are each independently hydrogen, a straight-chain, branched or cyclic alkyl, alkoxy, alkoxyalkyl, thioalkoxy group having from 1 to 20 carbon atoms $C_4$-$C_{18}$-aryl or $C_2$-$C_{10}$-alkenyl, in each of which one or more hydrogen atoms is optionally replaced by Cl, F or CN.

8. The material as claimed in claim 5, wherein said material is a homo- or copolymer based on PPV.

9. The material as claimed in claim 1, wherein said material is a homo- or copolymer based on polyspiro containing at least one group of the formula (A).

10. The material as claimed in claim 5, wherein said material is a homo- or copolymer based on polyspiro.

11. The material as claimed in claim 1, wherein said material is a low molecular weight compound having a 3-dimensional spirobifluorene structure containing at least one group of the formula (A).

12. The material as claimed in claim 5, wherein said material is a low molecular weight compound having a 3-dimensional spirobifluorene structure.

13. The material as claimed in claim 1, wherein said material is a low molecular weight compound having a 3-dimensional triptycene structure.

14. The material as claimed in claim 5, wherein said material is a low molecular weight compound having a 3-dimensional triptycene structure.

15. The material as claimed in claim 1, wherein said material is a derivative of quinacridone.

16. The material as claimed in claim 5, wherein said material is a derivative of quinacridone.

* * * * *